(12) United States Patent
Wu

(10) Patent No.: US 8,893,985 B2
(45) Date of Patent: Nov. 25, 2014

(54) PUMP FRAGRANCE DEVICE WITH A CARRIER AGENT

(75) Inventor: Henry Wu, New Taipei (TW)

(73) Assignee: Aromate Industries Co., Ltd., New Taipei (TW)

(*) Notice: Subject to any disclaimer, the term of this patent is extended or adjusted under 35 U.S.C. 154(b) by 308 days.

(21) Appl. No.: 13/303,300

(22) Filed: Nov. 23, 2011

(65) Prior Publication Data

US 2012/0132724 A1  May 31, 2012

(30) Foreign Application Priority Data

Nov. 26, 2010  (TW) .............................. 100114724 A

(51) Int. Cl.
*B05B 9/043* (2006.01)
*A61L 9/04* (2006.01)
*A61L 9/14* (2006.01)

(52) U.S. Cl.
CPC ... *A61L 9/04* (2013.01); *A61L 9/14* (2013.01); *A61L 2209/134* (2013.01)
USPC .............. 239/333; 239/34; 239/57; 239/289; 239/326; 239/337; 239/499; 422/123; 222/182; 222/192; 222/402.17

(58) Field of Classification Search
USPC ............. 239/34, 57, 289, 326, 333, 337, 499, 239/504; 422/123; 222/182, 192, 402.17
See application file for complete search history.

(56) References Cited

U.S. PATENT DOCUMENTS

| 4,084,732 | A | * | 4/1978 | Dearling | ........................ 239/326 |
| 4,200,229 | A | * | 4/1980 | Spector | ........................... 239/57 |
| 7,909,264 | B2 | * | 3/2011 | Dunne et al. | ................... 239/337 |

* cited by examiner

*Primary Examiner* — Steven J Ganey
(74) *Attorney, Agent, or Firm* — Juan Carlos A. Marquez; Bacon & Thomas PLLC

(57) ABSTRACT

A pump fragrance device includes a pump spray, an inner housing connected to a spray head, and an outer housing on the inner housing. On the inner housing, a junction piece connected to the spray head has an opening thereon. The inner housing's surface has an assembling piece to fit with the outer housing, which has an assembling structure to fit with the inner housing. The inner and outer housings form a fixing structure. The fixing structure is filled with a volatile carrier agent, at least a part of which is located in the spray path of the pump spray. When used, the pump spray sprays content onto a surface of the volatile carrier agent, thereby reducing the quantity of the volatile aromatic agent used. This prolongs the diffusion time of the volatile aromatic agent, thereby relieving users from the danger of the fragrance device being under high temperature.

9 Claims, 8 Drawing Sheets

PUMP FRAGRANCE DEVICE WITH A CARRIER AGENT

BACKGROUND OF THE INVENTION

1. Field of the Invention

The present invention relates to a fragrance device and, in particular, to a pump fragrance device with a carrier agent and such is capable of adjusting the emitting direction to achieve an evenly distributed and long-lasting scent within the environment in which the volatile aromatic agent is released.

2. Description of the Related Art

The use of a fragrance device in everyday life to allow the air within a home to be fresh and inviting has become a habitual practice to most people.

In a typical fragrance device, a liquid or colloidal aromatic agent is placed within a container, in which the aromatic agent is diffused through pores on the container or through an absorbing device that can soak in the aromatic agent via capillary action and emit such into the environment beyond the container.

However, this type conventional fragrance device cannot control the timing of the distribution of the aromatic agent. As soon as the seal is removed, the fragrance device is in use and the aromatic agent will be diffused into the air at a steady rate. For a consumer, when the consumer is not at the location where the fragrance device is placed, the fact that the fragrance device will still continuously release the aromatic agent into the adjacent environment is a meaningless waste.

In order to resolve this problem, fragrance device with a valve switch structure emerges in the market. On this fragrance device, a valve switch structure is positioned over pores, or an absorbing device, and when the fragrance device is not in use, the valve can be closed, thereby avoiding or slowing down the spreading and wasting of the aromatic agent. However, there is generally a small gap by the junction point due to the hinge of the valve or the shape of the container, so a completely air-tight seal is difficult to achieve; therefore, the aromatic agent in fact is still continuously being released via that small gap.

Unlike a valve structure, a metal high-pressure spray may be a more efficient device to store a volatile substance. Therefore, a fragrance device, wherein a volatile aromatic agent is stored in a high-pressure spray, is created and a user can spray the aromatic agent into the adjacent environment when needed. A typical high-pressure spray-style fragrance device generally includes a high-pressure gas cylinder and an outer housing to house the high-pressure gas cylinder. Within the high-pressure gas cylinder, there is a volatile propelling agent or a high-pressured compressed gas and the volatile aromatic agent. When the spray head is pressed, the volatile aromatic agent and the high-pressured gas are released into the environment. Thus, in addition to housing the high-pressure gas cylinder, the outer housing is also equipped with a device that presses down on the spray head, allowing the user to press on the spray head of the high-pressure gas cylinder with ease.

However, compared with a conventional fragrance device where the aromatic agent can continuously being diffused via pores or an absorbing device, the method of directly spraying the volatile aromatic agent into the environment lasts for a relatively shorter amount of time, although the effect of distributing the volatile aromatic agent can be quickly achieved. Moreover, the volatile aromatic agent contained within a high-pressure gas cylinder has a maximum concentration and maximum volume limitation due to the structure of the high-pressure gas cylinder. If a volatile aromatic agent is filled in overly high concentration making the volatile aromatic agent overly viscosity, or if the propelling agent is insufficiently filled, issues such as the volatile aromatic agent cannot be sprayed to form a mist and possibly even the situation in that the volatile aromatic agent cannot spurt out may occur. Therefore, only a relatively lower quantity of volatile aromatic agent can be stored within the high-pressure gas cylinder. The usage of such is not environmentally friendly as the high-pressure gas cylinder cannot be re-used, which is far from the current high popularized concept of recycling.

Moreover, depending on the different propelling agents used in the high-pressure gas cylinders, a high-pressure gas cylinder may explode under high temperature, but at a temperature that is too low, the propelling agent may not successfully gasify to create the jetting effect. Therefore, in view of the disadvantages of the above-noted types of fragrance devices, it is necessary to improve on the structure of the existing fragrance device.

SUMMARY OF THE INVENTION

Accordingly, an objective of the present invention is to provide a pump fragrance device with a carrier agent, where the volatile carrier agent is assembled onto the pump fragrance device. It is capable of adjusting the emitting direction, thereby providing a more pleasant experience to a user. Allowing the volatile carrier agent to absorb the volatile aromatic agent, the effect of prolonging the volatile aromatic agent's airborne time can be achieved.

Another objective of the present invention is to provide a pump fragrance device capable of storing the volatile aromatic agent. A user can decide at what point in time to emit the volatile aromatic agent. When such release is not needed, the fragrance device can be stored in a completely air-tight state to avoid wastage. By not using a high-pressure gas cylinder or a propelling agent, this invention is reducing the amount of resource wasted, and avoiding the problems associated with the high-pressure gas cylinder at high and low temperatures.

In order to achieve the above-noted objectives, the present invention provides a pump fragrance device with a carrier agent, comprising a pump spray, an inner housing that is connected to a spray head of the pump spray, and an outer housing that wraps around the inner housing, wherein the inner housing and the outer housing are assembled together to form a fixing structure. The fixing structure is fitted with a volatile carrier agent, and wherein at least part of volatile carrier agent is located on the spray path of the pump spray.

At the top of the inner housing is disposed with a junction piece that is fitted and connected to the spray head; the junction piece is disposed with a jet mouth and the jet mouth has an opening communicating with the spray head of the pump spray, so the alignment thereby allows the content within the pump spray to pass through without obstruction. The outer surface of the inner housing is disposed with an assembling piece such that it can be assembled to fit the outer housing. The outer housing is disposed with an assembling structure such that it can be assembled to fit the inner housing in order that when the inner housing and the outer housing are assembled together, it shall jointly form the fixing structure.

In a preferred embodiment, the junction piece is configured as an annular fixing wall to fit with the spray head, and the surface of the annular fixing wall is configured as a wedge-shaped surface structure to fit the spray head, so that a tightly fitted state is formed when the junction piece is nested on the spray head.

In another preferred embodiment, on one side of the annular fixing wall is disposed with a fixing hole and on the surface of the spray head is disposed with a spray nozzle to spray the content within, by making the spray nozzle to configure as a tubular structure such that it can fit the fixing hole.

In a preferred embodiment, the assembling piece is configured as an annular wall, and the outer surface of the annular wall is configured as a wedge-shaped surface structure, so that a tightly fitted state is formed when the assembling piece is assembled with the outer housing.

In another preferred embodiment, on the surface of the outer housing is disposed with a fixing part such that it can be fixed to a wall.

In a preferred embodiment, the outer housing is configured as a sleeve-shaped structure in which is to fit the outside surface of the inner housing. The fixing structure shall be an accommodating capacity jointly formed by the outer housing and the inner housing, and such said capacity is to be filled with the volatile carrier agent.

In a preferred embodiment, at the top of the outer housing is to position a screw cap and on the surface of the outer housing is disposed with at least one vent pores to facilitate diffusion of the volatile aromatic agent.

To model from the structure of the pump spray, the present invention can ensure that the volatile aromatic agent is kept in a completely air-tight state when not in use, thereby to avoid wasting the volatile aromatic agent. By spraying the volatile aromatic agent on the volatile carrier agent and allowing such to naturally diffusion rather than the mist spray method, the volatile aromatic agent can be at a relatively high concentration; thereby it is more efficient with the quantity of the volatile aromatic agent used and reducing the size of the fragrance device. Furthermore, without using any propelling agents or compressed gas, a user can be relieved from any worries relating to the danger of having the fragrance device under high temperature.

BRIEF DESCRIPTION OF THE DRAWINGS

The invention will be described according to the appended drawings.

PREFERRED EMBODIMENT OF THE PRESENT INVENTION

In order to make the construction, the use and the features of the present invention more clearly and comprehensible, the present invention is described in detail below with reference to the preferred embodiments and the accompanying drawings.

Figure 1:
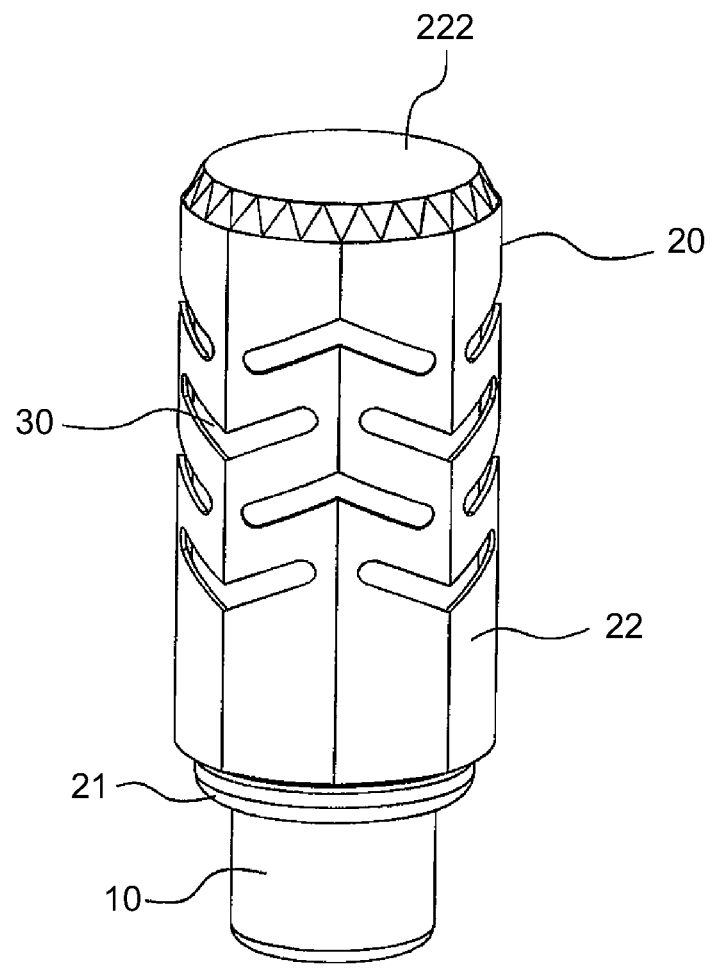
FIG. 1 is a perspective view of the present invention.
Figure 2:
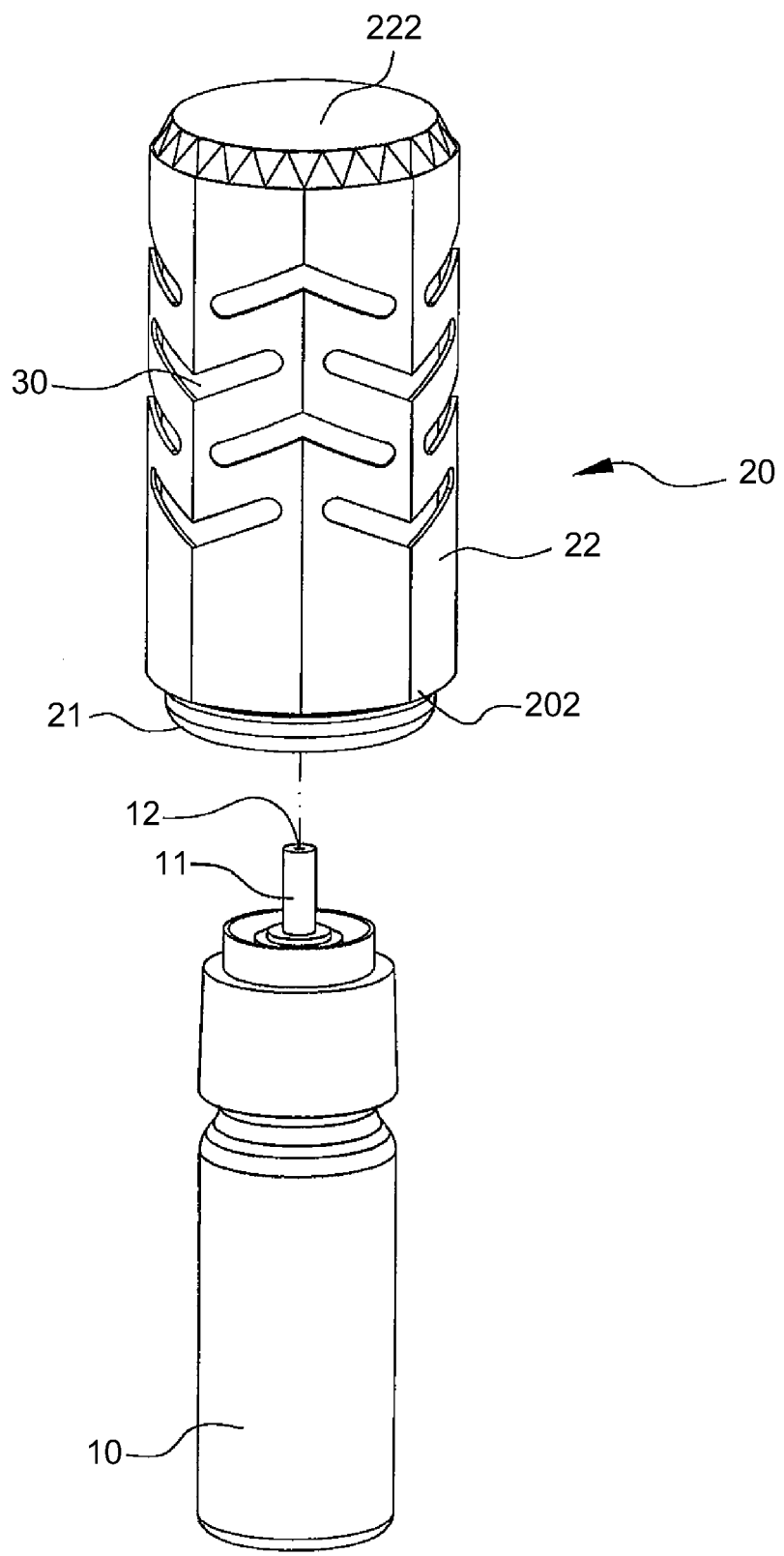
FIG. 2 is a schematic assembled view of the pump spray and the exterior structure shown in FIG. 1.
Figure 3:
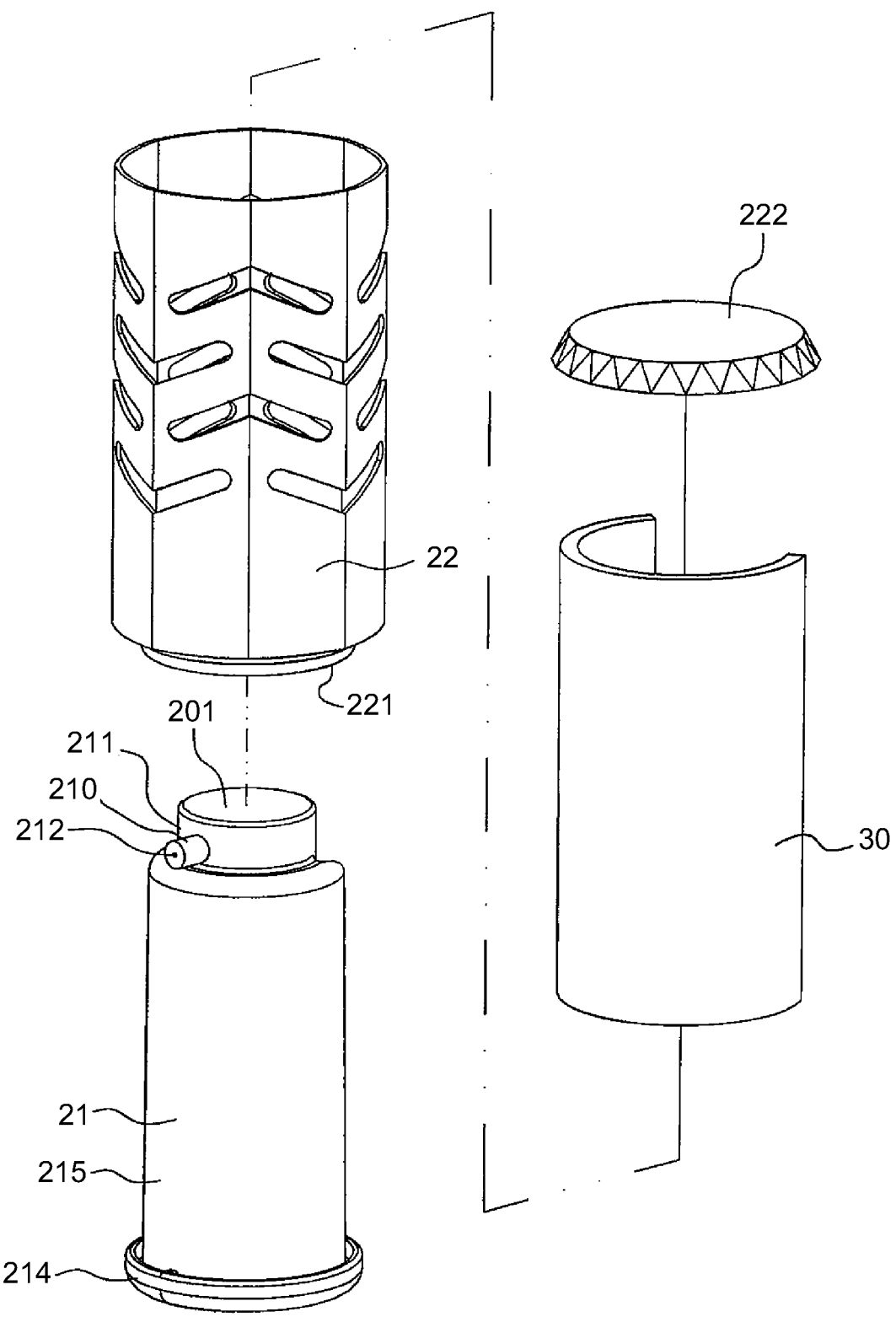
FIG. 3 is a assembled view of the elements within the exterior structure shown in FIG. 2.
Figure 4:
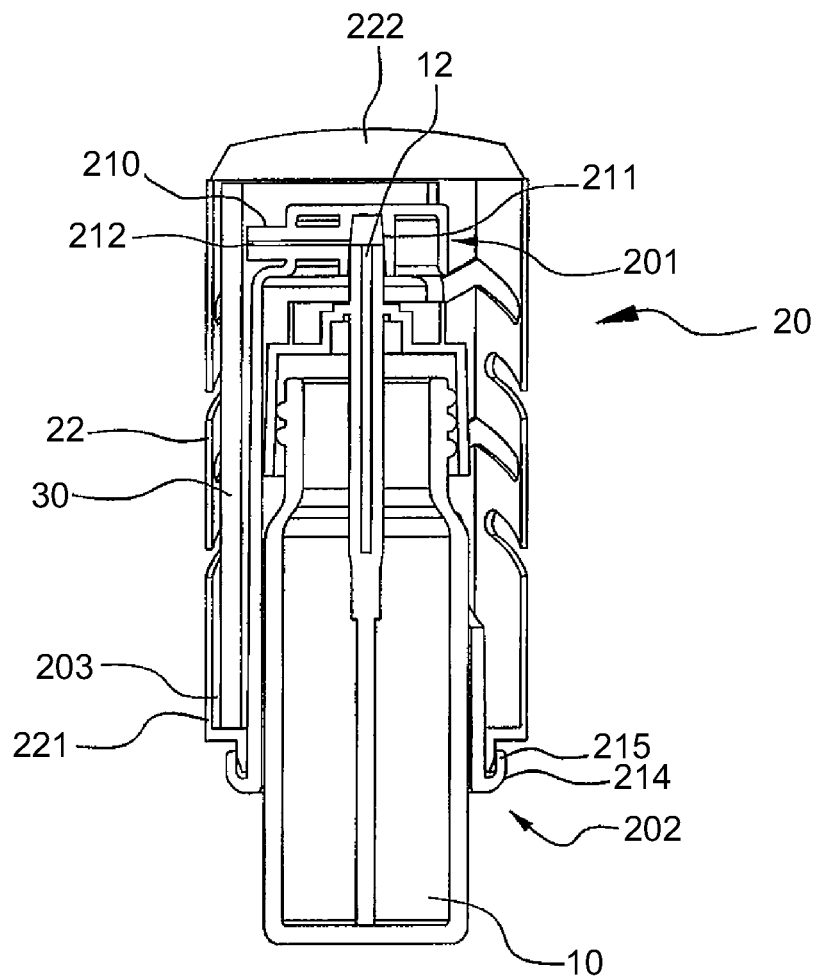
FIG. 4 is a schematic sectional view of the present invention.

Referring to FIG. 1 to FIG. 3, a pump fragrance device with a carrier agent of the present invention includes a pump spray 10 and an exterior structure 20 that is connected with the pump spray 10. Within the exterior structure 20 there is an inner housing 21 that is connected with a spray head 11 located on the pump spray 10, an outer housing 22 that wraps around the outer surface of the inner housing 21, and a volatile carrier agent 30 that is placed in between the outer housing 22 and the inner housing 21.

Figure 7:
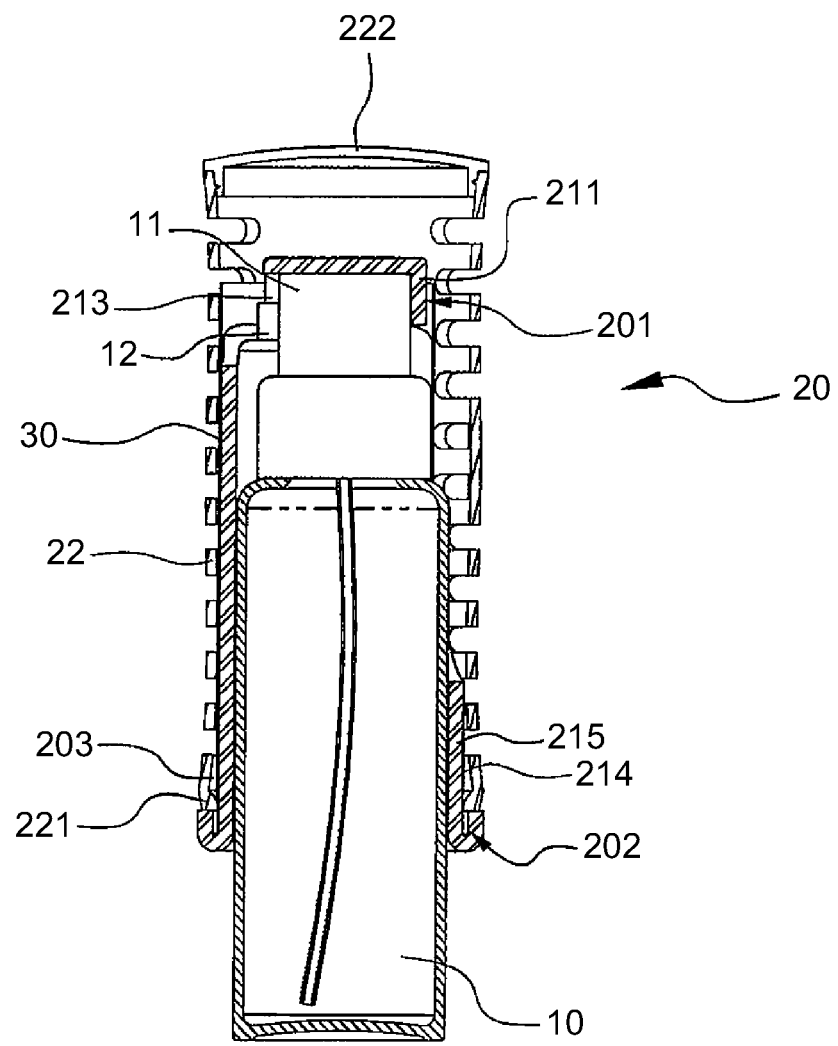
FIG. 7 is a schematic sectional view of another feasible embodiment.
Figure 8:
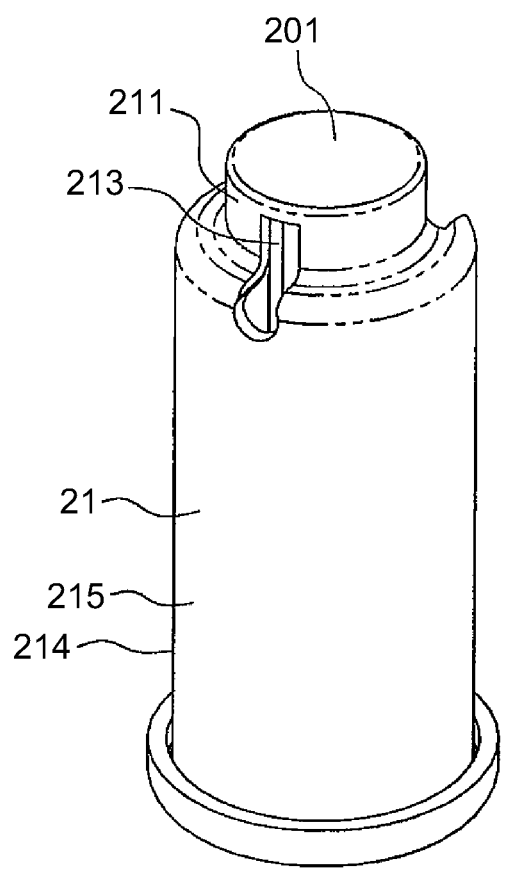
FIG. 8 is a perspective view of the inner housing shown in FIG. 7.

On the top of the inner housing 21 is disposed with a junction piece 201, fitted and connected to the spray head 11. On the surface of the junction piece 201 is disposed with a jet mouth 210. The jet mouth 210 has an opening 212 that communicates with the spray head 11, allowing the content sprayed by the spray head 11 be guided onto the volatile carrier agent 30. On the surface of the inner housing 21 is disposed with an assembling piece 214 that is to be fitted and connected to the outer housing 22.

The outer housing 22 is disposed with an assembling structure 221 that is to be fitted and connected to the inner housing 21. The inner housing 21 and the outer housing 22 when assembled together is to form a fixing structure 202. In this preferred embodiment, the fixing structure 202 is the accommodating capacity 203 created in between the inner housing 21 and the outer housing 22, so that such fixing structure 202 accommodates the volatile carrier agent 30, so that at least part of the volatile carrier agent 30 is located on the spray path of the pump spray 10.

Referring to FIG. 3 and FIG. 4, the junction piece 201 includes an annular fixing wall 211 that is fitted to the spray head 11 and the inner wall surface of the annular fixing wall 211 is configured as a wedge-shaped surface structure, so that the a tightly fitted state is formed when the spray head 11 is fixed within the junction piece 201. As the junction piece 201 is disposed with the jet mouth 210 and the jet mouth 210 has the opening 212, the content sprayed by the spray head 11 will be guided onto the volatile carrier agent 30.

Referring to FIG. 4, as shown in the figure, the junction piece 201 integrally extends downwards to form an annular wall 215, and at the bottom edge of the annular wall 215 is disposed with an assembling piece 214 that is to be fitted and connected to the outer housing 22; the assembling piece 214 is configured to have a groove to house the annular wall 215.

The outer housing 22 is configured as a sleeve-shaped structure to fit to the exterior of the inner housing 21. At the bottom of the outer housing 22 is disposed with an assembling structure 221 that is to be connected to the inner housing 21. The assembling structure 221 is configured as an annular flange with a wedge-shaped surface, so that a tightly fitted state can be naturally formed when the assembling structure 221 is nested within the groove. Additionally, the outer housing 22 and the inner housing 21 are jointed together to form the fixing structure 202. In this preferred embodiment, the fixing structure 202 forms the accommodating capacity 203 where the volatile carrier agent 30 is housed so that the volatile carrier 30 is fixed on the spray path of the spray head 11.

In an embodiment, as shown in the figure, on the top of the outer housing 22 is further disposed with a screw cap 222 capable of being open and close freely, allowing a user to place the volatile carrier agent 30 within the accommodating capacity 203 with ease. Additionally, on the surface of the outer housing 22 is disposed with at least one vent pore, allowing the volatile aromatic agent to diffuse. Persons of skilled in the art can easily establish that the outer housing 22 can be designed differently. For example, the outer housing 22 can have an integrated non-detachable screw cap 222, or the outer housing 22 may be designed as multiple parts that can be assembled to have multiple external looks or multiple ways to assemble such.

The above outer housing 22 and the inner housing 21 are provided to facilitate the understanding an embodiment of the present invention. In another preferred embodiment shown in FIG. 7 and FIG. 8, on the surface of the spray head 11 is a spray nozzle 12 that is capable of guiding the direction in which to spray the content; the opening is the fixing hole 213 that takes the shape of a long longitudinal hole structure. In this feasible embodiment, the fixing hole 213 not only allows the spray nozzle 12 to laterally extend outwards beyond the inner housing 21 to prevent the spray nozzle 12 from being obstructed when spraying the content, but also functions to fix the spray head 11 to prevent the spray nozzle 12 from rotating.

Figure 5:
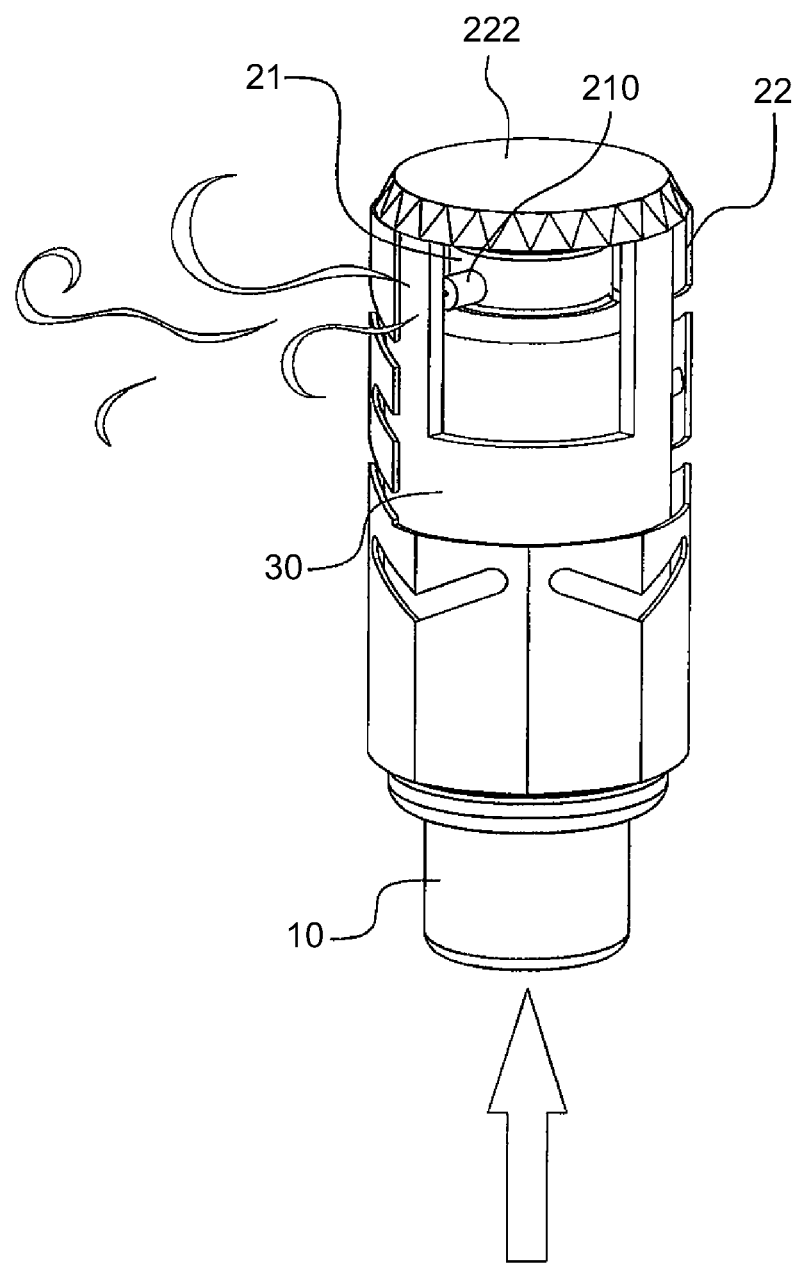
FIG. 5 is a schematic view of the usage of the present invention.
Figure 6:
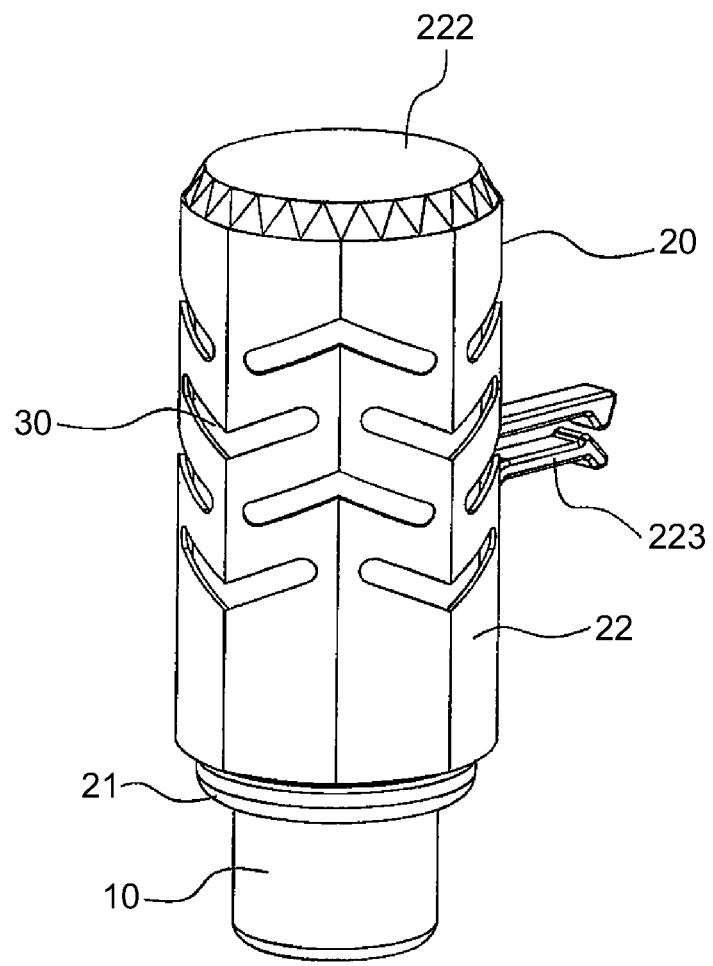
FIG. 6 is a perspective view of the another embodiment where a fixing part is added.

Referring to FIG. 5 and FIG. 6, in the preferred embodiment shown in the figures, the surface of the outer housing 22 further extends outwards to be disposed with a fixing part 223, allowing the fixing part 223 to fix the pump fragrance device to a wall or any other fixture where a user wants to place the fragrance device. The fixing part 223 may take any of the following forms: a clamping structure, a hook structure, a pasting structure, a magnetic structure, a snapping structure, an sucking structure, and a hook and loop structure. As shown in FIG. 5 and FIG. 6, the shown embodiment has the fixing part 223 as a clamping structure. When a user wants the fragrance device to be in use, the user can directly press on the bottom of the pump spray 10, so that the volatile aromatic agent is sprayed onto the volatile carrier agent 30, allowing the volatile aromatic agent, via the volatile carrier agent 30, to gradually spread in the adjacent environment.

To sum up, through modifying the structure of the pump spray, the present invention is able to actually control the quantity of the volatile aromatic agent used, thereby to avoid wasting the volatile aromatic agent. The volatile aromatic agent is sprayed onto the volatile carrier agent, allowing such to naturally diffuse rather than the mist spray approach, so that the volatile aromatic agent can be of a relatively high concentration, thereby saving quantity of the fragrant volatile agent used and reducing the size of the fragrance device.

The embodiments above are provided only to conveniently describe the present invention but do not limit the present invention. Simple variations and modifications made by persons skilled in the art according to the claims and specification of the present invention shall be deemed as falling within the gist and scope of the present invention and all such shall fall within the appended claims.

What is claimed is:

1. A pump fragrance device with a carrier agent, comprising a pump spray, an inner housing that is connected to a spray head on the pump spray, and an outer housing that wraps around the outer surface of the inner housing, wherein the inner housing and the outer housing are assembled together to form a fixing structure, and the fixing structure is fitted with a volatile carrier agent, wherein at least part of volatile carrier agent is located on the spray path of the pump spray, wherein a junction piece is located at and integrated into the top of the inner housing, the junction piece is further fitted and connected to the spray head and formed with an opening disposed on the spray head, the outer surface of the inner housing is equipped with an assembling piece to be assembled to fit the outer housing, the outer housing is equipped with an assembling structure to be assembled to fit the assembling piece, so through assembling the assembling piece and the assembling structure, the inner housing and the outer housing jointly form the fixing structure, the junction piece is configured as an annular fixing wall to fit the spray head, and the surface of the annular fixing wall is configured as a wedge-shaped surface structure to fit the spray head, so that a tightly fitted state is formed after the junction piece is nested on the spray head.

2. The pump fragrance device with a carrier agent according to claim 1, wherein the opening is configured as a fixing hole, and on the surface of the spray head is disposed with a spray nozzle to spray content within, where the spray nozzle is configured as a tubular structure fitted and connected to the fixing hole.

3. The pump fragrance device with a carrier agent according to claim 1, wherein the assembling piece is configured as an annular wall, and the outer surface of the annular wall is configured as a wedge-shaped surface structure, so that a tightly fitted state is formed after the assembling piece is assembled with the outer housing.

4. The pump fragrance device with a carrier agent according to claim 1, wherein the outer housing is configured as a sleeve-shaped structure to fit and wrap around the outer surface of the inner housing.

5. The pump fragrance device with a carrier agent according to claim 4, wherein the fixing structure is configured as an accommodating capacity jointly formed by the outer housing and the inner housing, and the accommodating capacity is filled with the volatile carrier agent.

6. The pump fragrance device with a carrier agent according to claim 4, wherein on the top of the outer housing is disposed with a screw cap.

7. The pump fragrance device with a carrier agent according to claim 1, wherein the surface of the outer housing is disposed with a fixing part to be fixed to a wall.

8. The pump fragrance device with a carrier agent according to claim 7, wherein the fixing part takes any of the following forms: a clamping structure, a hook structure, a pasting structure, a magnetic structure, a snapping structure, an sucking structure, and a hook and loop structure.

9. The pump fragrance device with a carrier agent according to claim 1, wherein a surface of the outer housing is disposed with at least one vent pore.

* * * * *